(12) United States Patent
Nishihara

(10) Patent No.: US 9,998,641 B2
(45) Date of Patent: Jun. 12, 2018

(54) IMAGE PICKUP UNIT PROVIDED IN ENDOSCOPE

(71) Applicant: OLYMPUS CORPORATION, Tokyo (JP)

(72) Inventor: Teruyuki Nishihara, Musashino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/350,257

(22) Filed: Nov. 14, 2016

(65) Prior Publication Data

US 2017/0064164 A1    Mar. 2, 2017

Related U.S. Application Data

(63) Continuation of application No. PCT/JP2015/063611, filed on May 12, 2015.

(30) Foreign Application Priority Data

May 15, 2014    (JP) .................................. 2014-101649

(51) Int. Cl.
    *A61B 1/05*     (2006.01)
    *H04N 5/225*    (2006.01)
    (Continued)

(52) U.S. Cl.
    CPC ............. *H04N 5/2252* (2013.01); *A61B 1/00* (2013.01); *A61B 1/005* (2013.01); *A61B 1/0008* (2013.01);
    (Continued)

(58) Field of Classification Search
    CPC ... A61B 1/00096; A61B 1/00163; A61B 1/05; G02B 23/243; G02B 7/025; G02B 7/028;
    (Continued)

(56) References Cited

U.S. PATENT DOCUMENTS 4,779,130 A * 10/1988 Yabe ...................... A61B 1/05
                                                        348/76
5,127,734 A *  7/1992 Ohi ..................... G01B 9/02052
                                                       356/514
(Continued)

FOREIGN PATENT DOCUMENTS

CN       103068295 A    4/2013
CN       103565392 A    2/2014
(Continued)

OTHER PUBLICATIONS

International Search Report dated Aug. 11, 2015 issued in PCT/JP2015/063611.
(Continued)

*Primary Examiner* — John P Leubecker
(74) *Attorney, Agent, or Firm* — Scully, Scott, Murphy & Presser, P.C.

(57) ABSTRACT

An optical unit includes: a lens holding frame configured to hold an objective optical system; an image pickup device holding frame configured to hold an image pickup device including a light receiving section that detects an object image formed by the objective optical system, to which a first holding frame is interpolated and fitted; a welding section provided on a fitting section of the lens holding frame and the image pickup device holding frame, configured to fix the lens holding frame and the image pickup device holding frame at a fitting position at which an image forming surface of the object image by the objective optical system and the light receiving section are made to coincide; and a bonding material configured to fill a gap formed between the lens holding frame and the image pickup device holding frame.

8 Claims, 16 Drawing Sheets

(51) Int. Cl.
    *A61B 1/00*   (2006.01)
    *G02B 23/24*  (2006.01)
    *G02B 23/26*  (2006.01)
    *A61B 1/005*  (2006.01)
    *A61B 1/04*   (2006.01)

(52) U.S. Cl.
    CPC ...... *A61B 1/00045* (2013.01); *A61B 1/00163* (2013.01); *A61B 1/04* (2013.01); *G02B 23/24* (2013.01); *G02B 23/2476* (2013.01); *G02B 23/26* (2013.01); *H04N 5/2253* (2013.01); *H04N 5/2254* (2013.01); *H04N 2005/2255* (2013.01)

(58) Field of Classification Search
    CPC .................. G02B 7/022; H04N 5/2254; H04N 2005/2255
    USPC ........................................................ 600/176
    See application file for complete search history.

(56) References Cited

U.S. PATENT DOCUMENTS

| | | | | |
|---|---|---|---|---|
| 6,328,691 | B1* | 12/2001 | Rudischhauser | A61B 1/0008 600/133 |
| 6,547,722 | B1* | 4/2003 | Higuma | A61B 1/00096 600/133 |
| 6,767,322 | B1* | 7/2004 | Futatsugi | A61B 1/00096 600/129 |
| 2002/0028049 | A1* | 3/2002 | Bartur | G02B 6/4202 385/92 |
| 2002/0037142 | A1* | 3/2002 | Rossi | G02B 6/4204 385/92 |
| 2002/0094169 | A1* | 7/2002 | Benator | G02B 6/32 385/55 |
| 2004/0176661 | A1* | 9/2004 | Futatsugi | A61B 1/05 600/110 |
| 2005/0089286 | A1* | 4/2005 | Hatori | A61B 1/00096 385/117 |
| 2005/0117048 | A1* | 6/2005 | Matsushita | B29C 65/561 348/340 |
| 2006/0077575 | A1* | 4/2006 | Nakai | B29C 65/1664 359/819 |
| 2007/0004965 | A1* | 1/2007 | Ogino | A61B 1/00096 600/110 |
| 2007/0008407 | A1* | 1/2007 | Yamamoto | A61B 1/05 348/65 |
| 2007/0118019 | A1* | 5/2007 | Mitani | A61B 1/00096 600/176 |
| 2008/0080051 | A1 | 4/2008 | Yamamoto | |
| 2009/0103193 | A1* | 4/2009 | Berube | G02B 7/02 359/819 |
| 2010/0076268 | A1* | 3/2010 | Takasugi | A61B 1/00177 600/171 |
| 2012/0133825 | A1* | 5/2012 | Nakajima | H04N 5/2253 348/374 |
| 2012/0293641 | A1* | 11/2012 | Nagamizu | A61B 1/00163 348/65 |
| 2014/0235947 | A1* | 8/2014 | Dahmen | A61B 1/00096 600/129 |

FOREIGN PATENT DOCUMENTS

| | | |
|---|---|---|
| JP | 2002-238837 A | 8/2002 |
| JP | 2005-021719 A | 1/2005 |
| JP | 2006-263064 A | 10/2006 |
| JP | 2008-079881 A | 4/2008 |

OTHER PUBLICATIONS

Japanese Office Action dated May 24, 2016 issued in Japanese Patent Application No. 2015-552665.
Extended Supplementary European Search Report dated Nov. 6, 2017 in European Patent Application No. 15 79 2995.1.

\* cited by examiner

FIG. 19
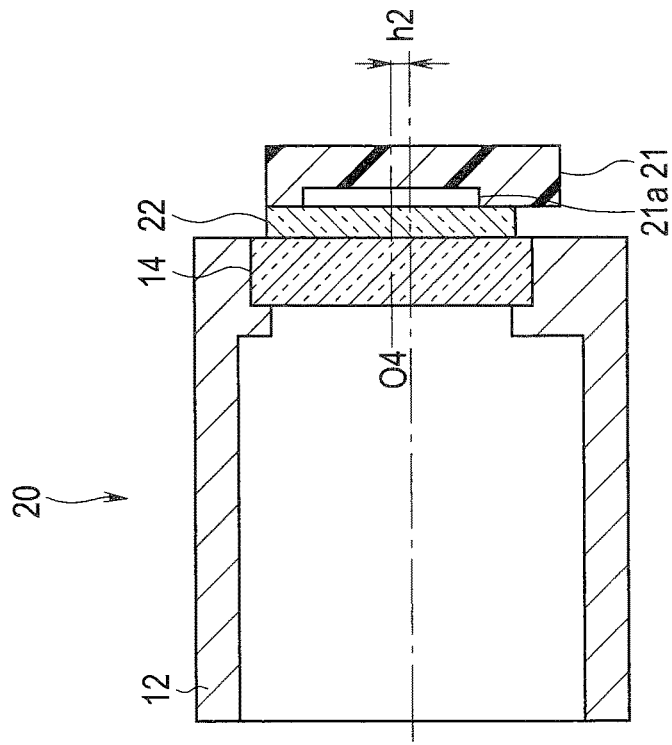
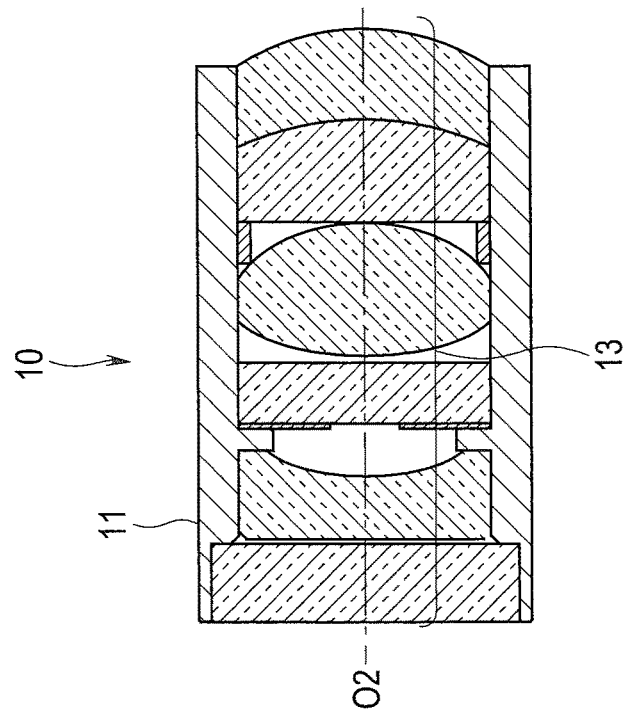

IMAGE PICKUP UNIT PROVIDED IN ENDOSCOPE

CROSS REFERENCE TO RELATED APPLICATION

This application is a continuation application of PCT/JP2015/063611 filed on May 12, 2015 and claims benefit of Japanese Application No. 2014-101649 filed in Japan on May 15, 2014, the entire contents of which are incorporated herein by this reference.

BACKGROUND OF THE INVENTION

1. Field of the Invention

The present invention relates to an optical unit that lens frame and device frame are fitted and fixed and an endoscope including the optical unit.

2. Description of the Related Art

An endoscope which can be introduced from outside of a living body or a structure to inside in order to observe a location where observation is difficult such as the inside of the living body or the inside of the structure, and includes an optical unit such as an image pickup unit for picking up an optical image is utilized in a medical field or an industrial field, for example.

The optical unit such as the image pickup unit of the endoscope includes an objective lens that forms an object image and an image pickup device such as a CCD (charge-coupled device) or a CMOS (complementary metal oxide semiconductor) generally disposed on an image forming surface of the objective lens.

As such an optical unit, for example, an image pickup unit disclosed in Japanese Patent Application Laid-Open Publication No. 2002-238837 is known, and generally a lens frame and a device frame are fitted to each other, and stuck and fixed by a thermosetting type adhesive or a bonding material by soldering of solder or the like.

SUMMARY OF THE INVENTION

An optical unit of one aspect of the present invention includes: a cylindrical lens holding frame configured to hold an objective optical system; a cylindrical image pickup device holding frame configured to hold an image pickup device including a light receiving section that detects an object image formed by the objective optical system, to which the lens holding frame is interpolated and fitted; a welding section and a non-welding section provided on a fitting section of the lens holding frame and the image pickup device holding frame and formed at an outer circumferential section of the image pickup device holding frame on a same plane vertical to an optical axis, configured to fix the lens holding frame and the image pickup device holding frame at a fitting position at which an image forming surface of the object image by the objective optical system and the light receiving section are made to coincide; and a bonding material configured to fill a gap formed between the lens holding frame and the image pickup device holding frame.

An endoscope of one aspect of the present invention includes an optical unit provided with: a cylindrical lens holding frame configured to hold an objective optical system; a cylindrical image pickup device holding frame configured to hold an image pickup device including a light receiving section that detects an object image formed by the objective optical system, to which the lens holding frame is interpolated and fitted; a welding section provided on a fitting section of the lens holding frame and the image pickup device holding frame and formed at an outer circumferential section of the image pickup device holding frame on a same plane vertical to an optical axis, configured to fix the lens holding frame and the image pickup device holding frame at a fitting position at which an image forming surface of the object image by the objective optical system and the light receiving section are made to coincide; and a bonding material and a non-welding section configured to fill a gap formed between the lens holding frame and the image pickup device holding frame, in which the welding section formed at the outer circumferential section of the image pickup device holding frame is formed at one location.

BRIEF DESCRIPTION OF THE DRAWINGS

FIG. 19 is a sectional view illustrating a state before the lens unit and the image pickup device unit are fitted in a second modification relating to the second embodiment;

DETAILED DESCRIPTION OF THE PREFERRED EMBODIMENT(S)

Figure 1:
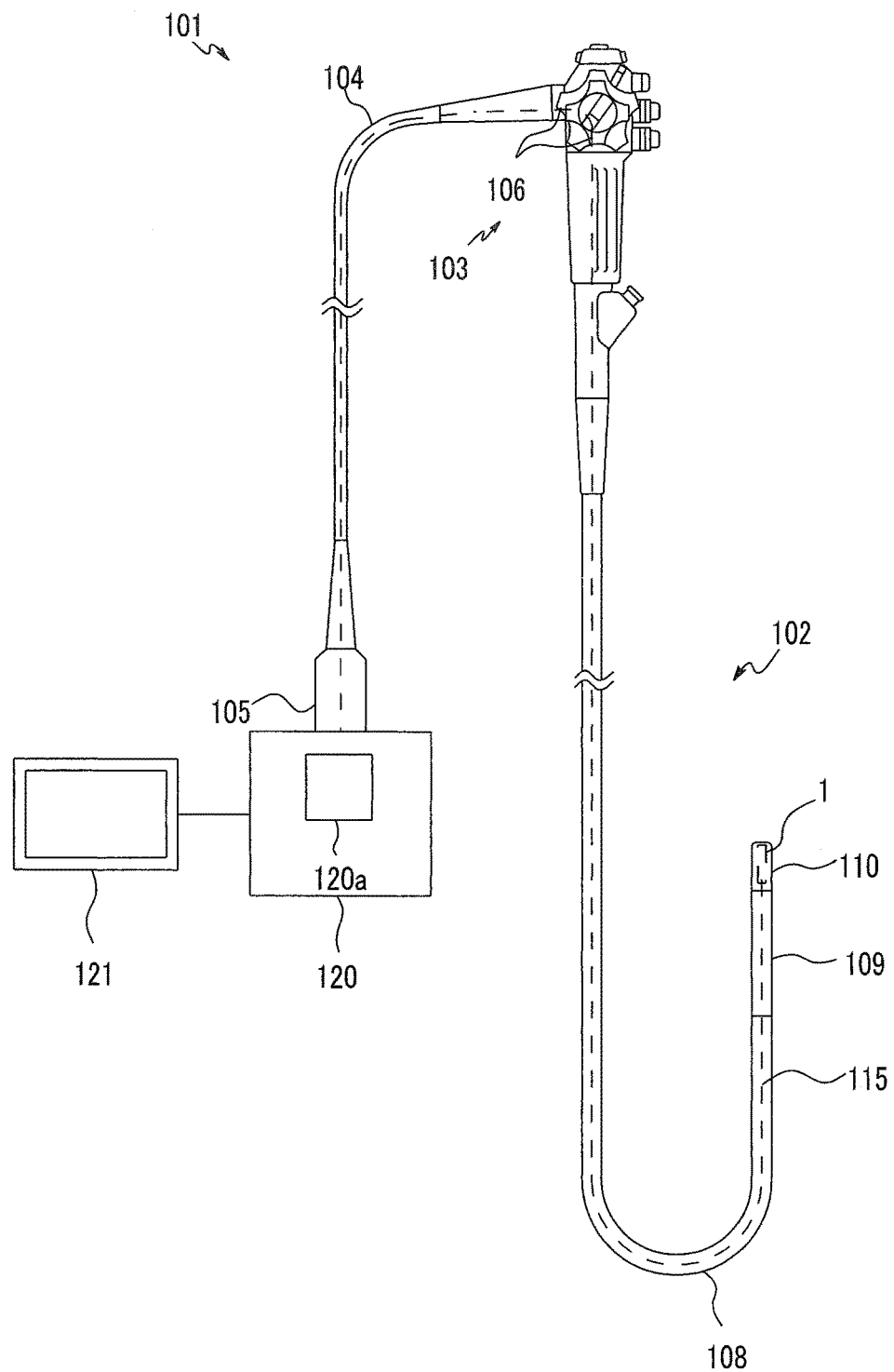
FIG. 1 is a diagram illustrating a configuration of an endoscope relating to a first embodiment.

Hereinafter, preferred forms of the present invention will be described with reference to the drawings. Note that, in the individual drawings used in the following description, a scale is made different for each component in order to turn the individual components to such sizes that the components can be recognized on the drawings, and the present invention is not limited only to quantities of the components, shapes of the components, ratios of the sizes of the components, and relative positional relationships of the individual components described in the drawings. In addition, in the following description, upper and lower directions in a view toward a paper surface of the drawing are sometimes described as an upper part and a lower part of the component.

First Embodiment

First, an optical unit and an endoscope of the first embodiment of the present invention will be described below, based on the drawings.

Figure 2:
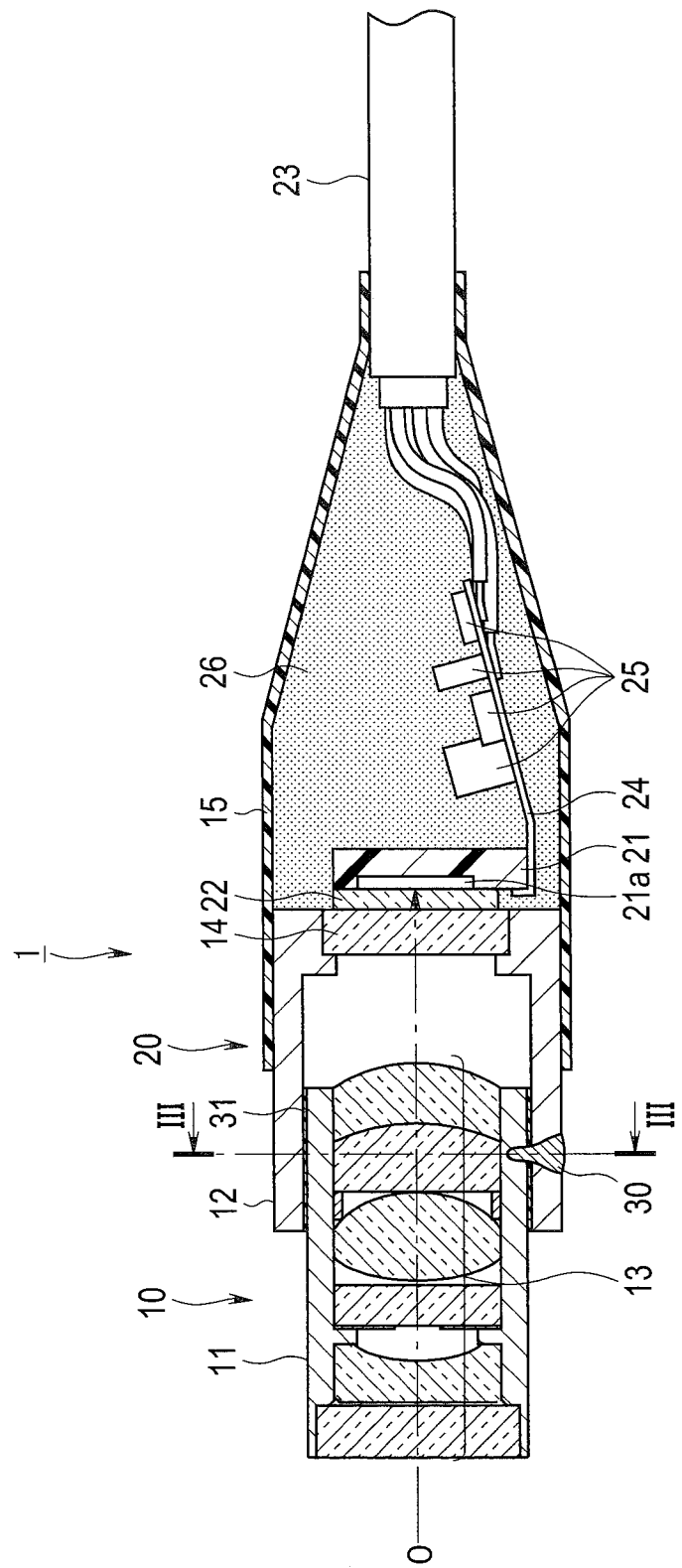
FIG. 2 is a sectional view illustrating a configuration of an image pickup unit relating to the first embodiment.
Figure 3:
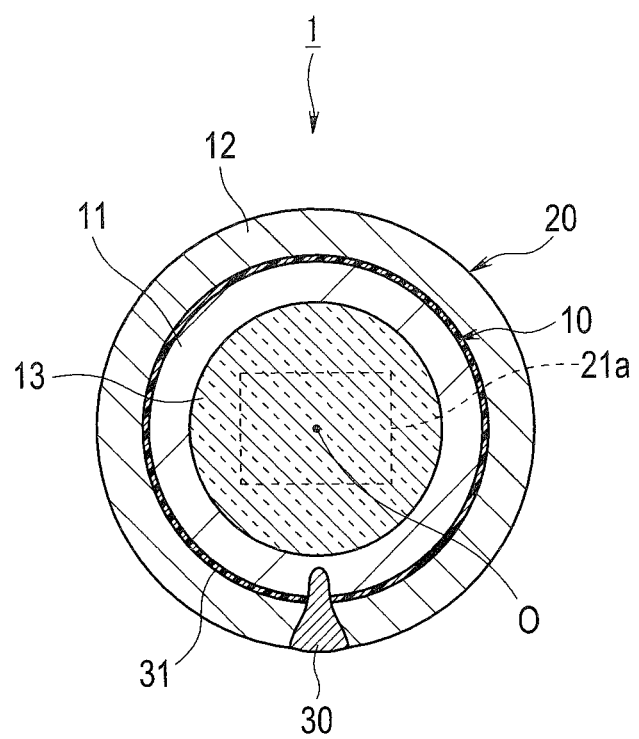
FIG. 3 is a sectional view illustrating a configuration of the optical unit along a III-III line in FIG. 2 relating to the first embodiment.
Figure 4:
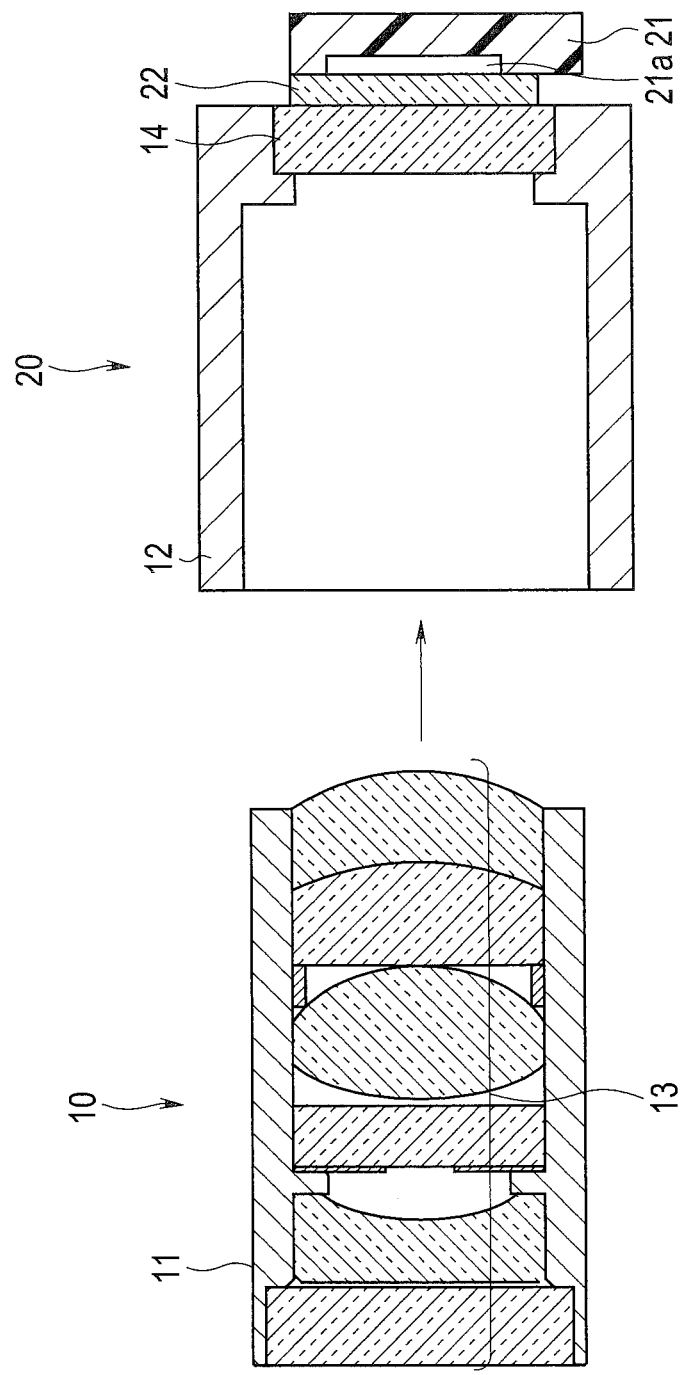
FIG. 4 is a sectional view illustrating a state before a lens unit and an image pickup device unit are fitted relating to the first embodiment.
Figure 5:
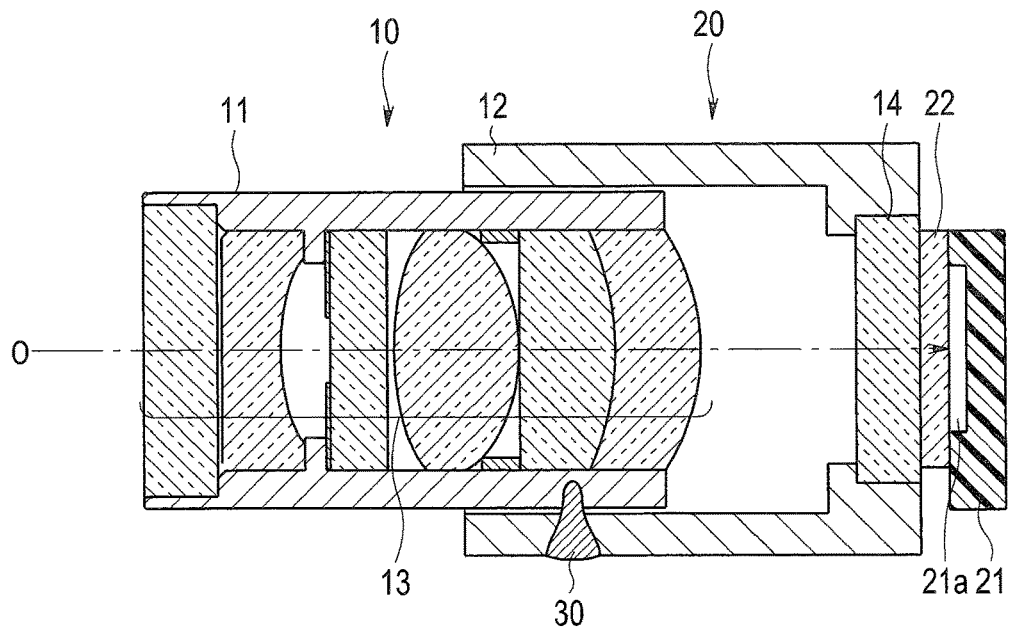
FIG. 5 is a sectional view illustrating a state that the lens unit and the image pickup device unit are fitted and fixed by a welding section relating to the first embodiment.
Figure 6:
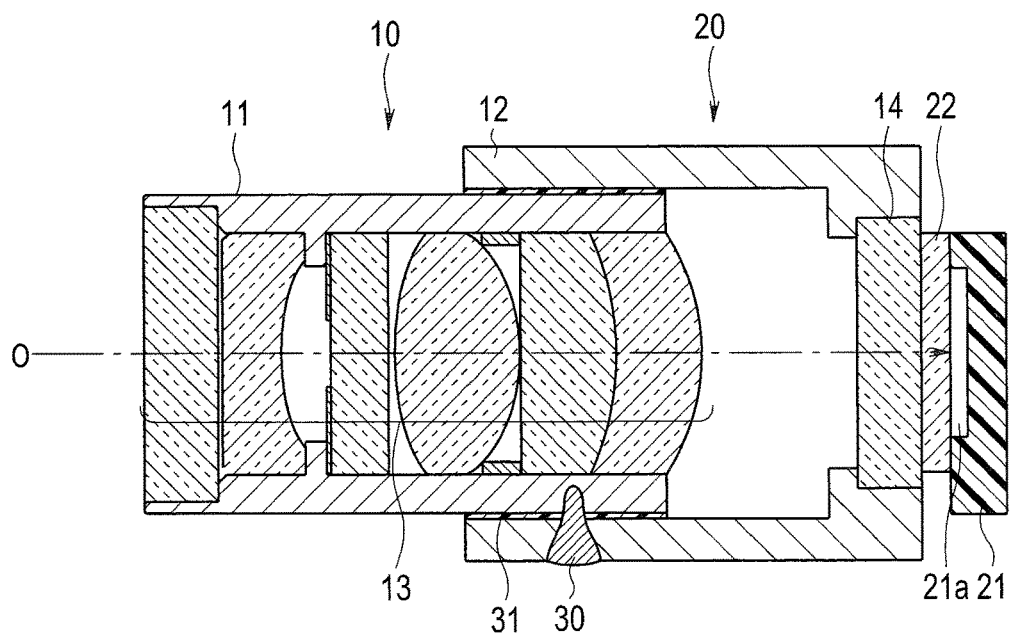
FIG. 6 is a sectional view illustrating a state that the lens unit and the image pickup device unit are fixed by a bonding material relating to the first embodiment.
Figure 7:
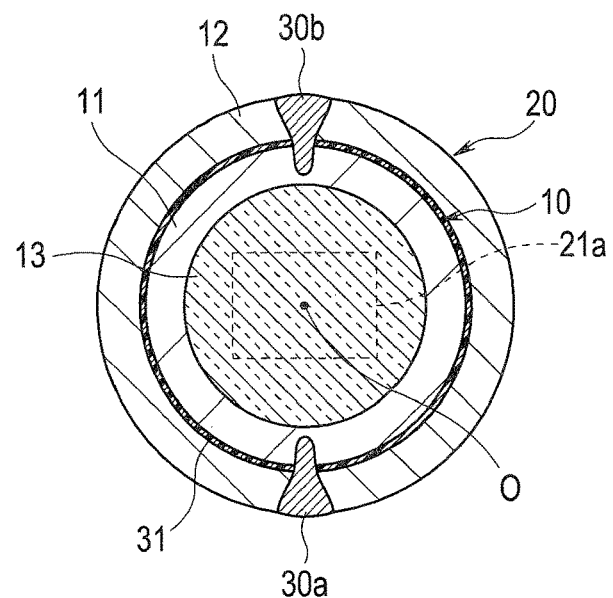
FIG. 7 is a horizontal sectional view illustrating a configuration of an optical unit in a first modification relating to the first embodiment.
Figure 8:
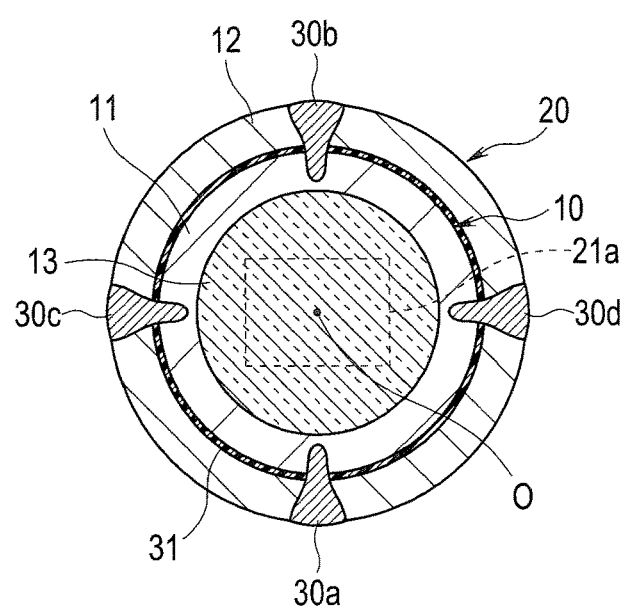
FIG. 8 is a horizontal sectional view illustrating a configuration of an optical unit in a second modification relating to the first embodiment.
Figure 9:
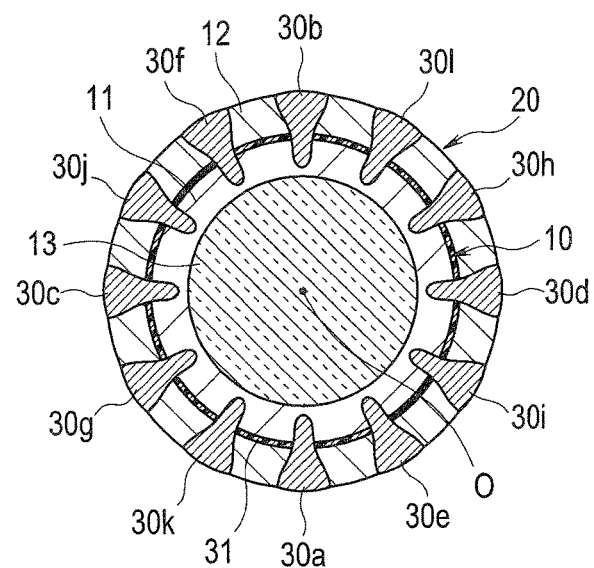
FIG. 9 is a horizontal sectional view illustrating a configuration of an optical unit in a third modification relating to the first embodiment.
Figure 10:
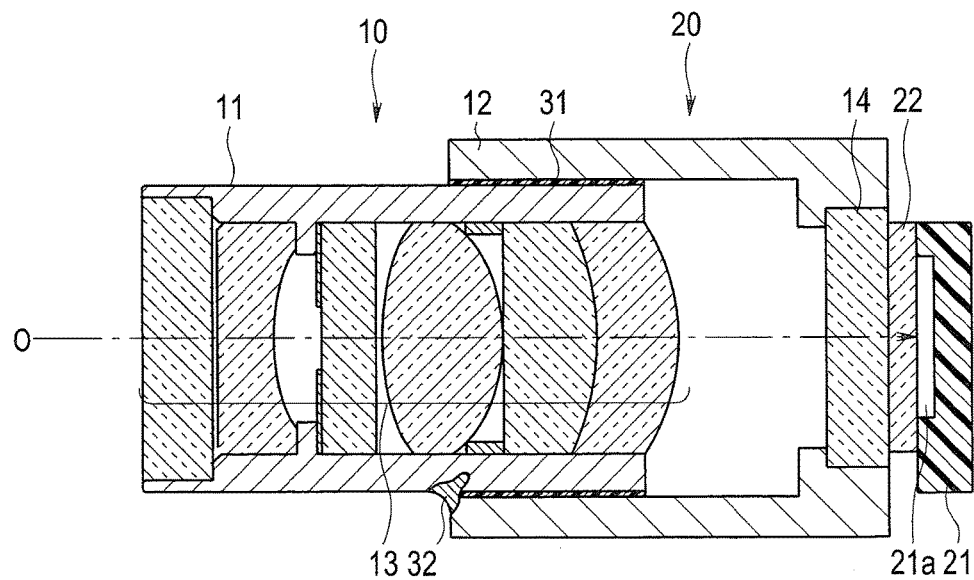
FIG. 10 is a vertical sectional view illustrating a configuration of an optical unit in a fourth modification relating to the first embodiment.
Figure 11:
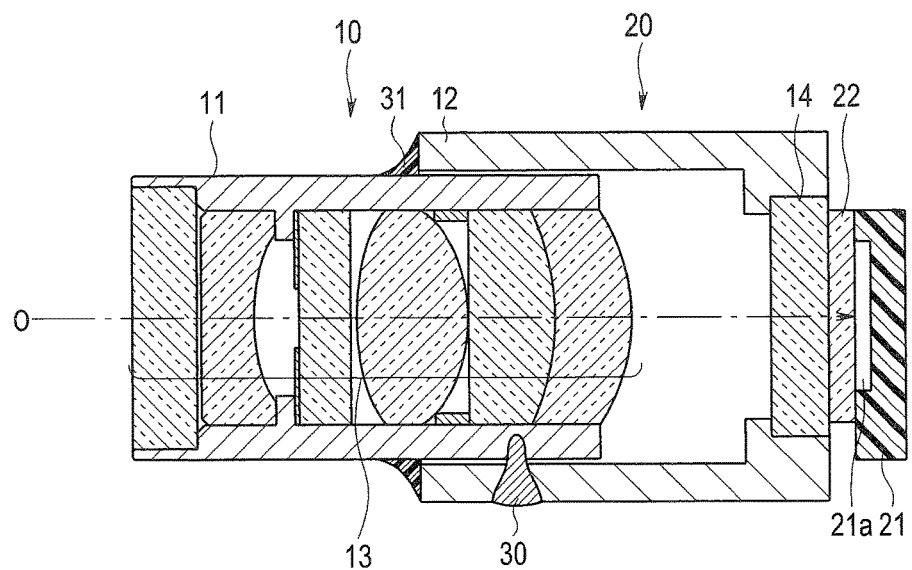
FIG. 11 is a vertical sectional view illustrating a configuration of an optical unit in a first reference example relating to the first embodiment.
Figure 12:
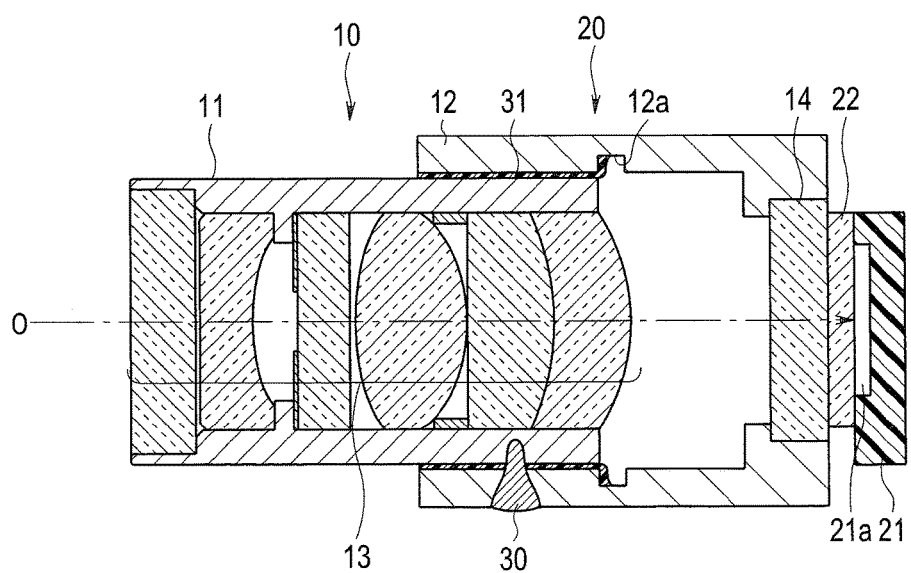
FIG. 12 is a vertical sectional view illustrating a configuration of an optical unit in a second reference example relating to the first embodiment.
Figure 13:
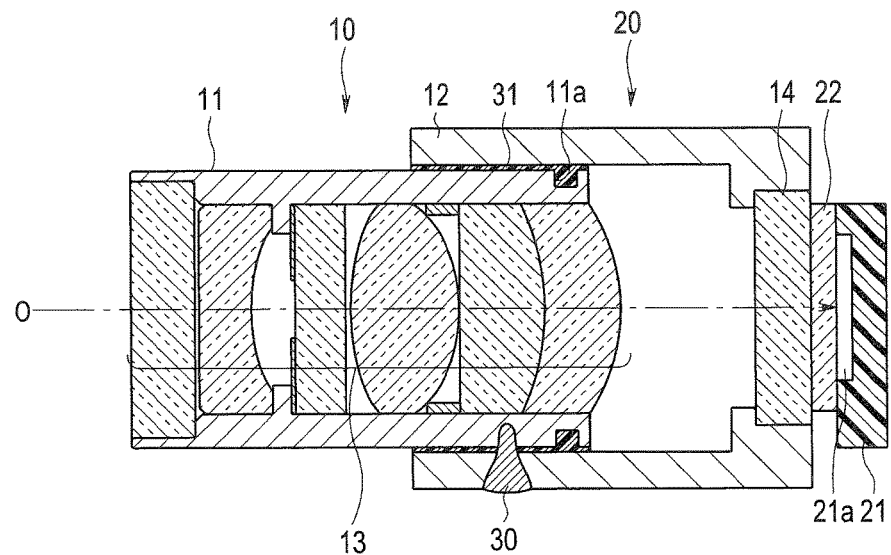
FIG. 13 is a vertical sectional view illustrating a configuration of an optical unit in a third reference example relating to the first embodiment.
Figure 14:
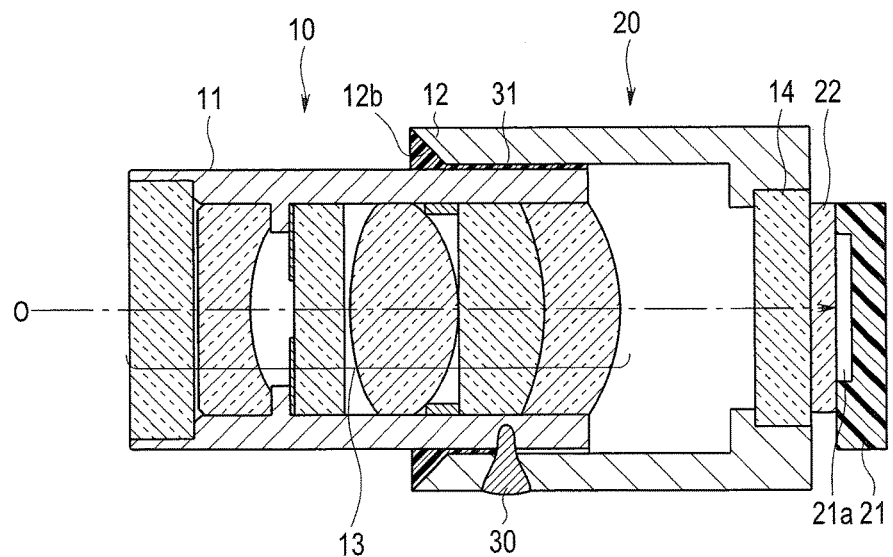
FIG. 14 is a vertical sectional view illustrating a configuration of an optical unit in a fourth reference example relating to the first embodiment.
Figure 15:
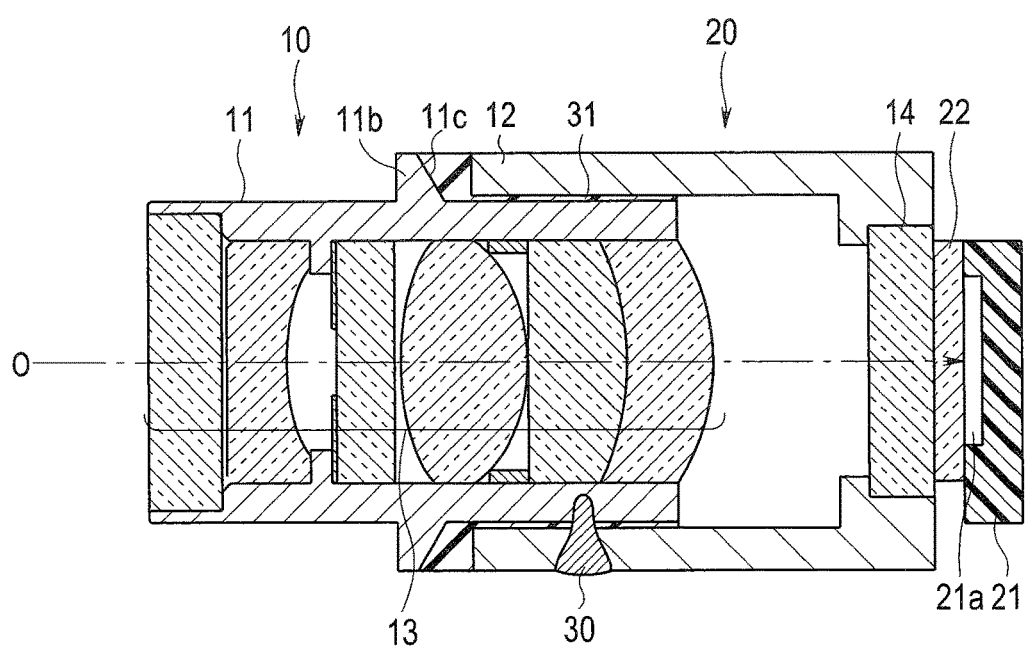
FIG. 15 is a vertical sectional view illustrating a configuration of an optical unit in a fifth reference example relating to the first embodiment.

Note that FIG. 1 is a diagram illustrating a configuration of an endoscope, FIG. 2 is a sectional view illustrating a configuration of an optical unit, FIG. 3 is a sectional view illustrating a configuration of the optical unit along a III-III line in FIG. 2, FIG. 4 is a sectional view illustrating a state before a lens unit and an image pickup device unit are fitted, FIG. 5 is a sectional view illustrating a state that the lens unit and the image pickup device unit are fitted and fixed by a welding section, FIG. 6 is a sectional view illustrating a state that the lens unit and the image pickup device unit are fixed by a bonding material, FIG. 7 is a horizontal sectional view illustrating a configuration of an optical unit in a first modification, FIG. 8 is a horizontal sectional view illustrating a configuration of an optical unit in a second modification, FIG. 9 is a horizontal sectional view illustrating a configuration of an optical unit in a third modification, FIG. 10 is a vertical sectional view illustrating a configuration of an optical unit in a fourth modification, FIG. 11 is a vertical sectional view illustrating a configuration of an optical unit in a first reference example, FIG. 12 is a vertical sectional view illustrating a configuration of an optical unit in a second reference example, FIG. 13 is a vertical sectional view illustrating a configuration of an optical unit in a third reference example, FIG. 14 is a vertical sectional view illustrating a configuration of an optical unit in a fourth reference example, and FIG. 15 is a vertical sectional view illustrating a configuration of an optical unit in a fifth reference example.

Hereinafter, one example of the embodiment of the present invention will be described. First, referring to FIG. 1, one example of a configuration of an endoscope 101 including an image pickup unit 1 as an optical unit relating to the present invention will be described.

The endoscope 101 of the present embodiment can be introduced into a subject such as a human body, and has a configuration of optically picking up an image of a predetermined observation site inside the subject.

Note that the subject into which the endoscope 101 is to be introduced is not limited to a human body and may be another living body or may be an artifact such as a machine or a structure.

The endoscope 101 is mainly configured by an insertion section 102, an operation section 103 positioned at a proximal end of the insertion section 102, and a universal cord 104 as a composite cable extending from a side part of the operation section 103.

The insertion section 102 is configured by continuously providing a distal end portion 110 disposed at a distal end, a freely bendable bending portion 109 disposed on a proximal end side of the distal end portion 110, and a flexible tube portion 108 disposed on the proximal end side of the bending portion 109, connected to the distal end side of the operation section 103 and provided with flexibility.

Note that the endoscope 101 may be the one of a form so called a rigid endoscope not provided with a part having flexibility in the insertion section 102.

Details will be described later, but the distal end portion 110 is provided with the image pickup unit 1. In addition, the operation section 103 is provided with an angle operation knob 106 for operating bending of the bending portion 109.

On a proximal end portion of the universal cord 104, an endoscope connector 105 to be connected to an external device 120 is provided. The external device 120 to which the endoscope connector 105 is to be connected is connected to an image display section 121 such as a monitor through a cable.

Note that the endoscope 101 includes an electric cable 115 inserted in the universal cord 104, the operation section 103 and the insertion section 102, and an optical fiber bundle (not shown in the figure) that transmits illumination light from a light source section provided in the external device 120.

The electric cable 115 is configured so as to electrically connect the endoscope connector 105 and the image pickup unit 1. By connecting the endoscope connector 105 to the external device 120, the image pickup unit 1 is electrically connected through the electric cable 115 to the external device 120.

Through the electric cable 115, power is supplied from the external device 120 to the image pickup unit 1 and communication between the external device 120 and the image pickup unit 1 is performed.

The external device 120 is provided with an image processing section. The image processing section generates video signals based on image pickup device output signals outputted from the image pickup unit 1, and outputs the video signals to the image display section 121. That is, in the present embodiment, an optical image (endoscope image) picked up by the image pickup unit 1 is displayed as a video at the image display section 121.

Note that the endoscope 101 is not limited to the configuration of being connected to the external device 120 or the image display section 121, and may be configured to include part or all of the image processing section or the monitor, for example.

In addition, the optical fiber bundle is configured to transmit light emitted from the light source section of the external device 120 to an illumination window as an illumination light emitting section of the distal end portion 110. Further, the light source section may be configured to be disposed at the operation section 103 or the distal end portion 110 of the endoscope 101.

Next, the configuration of the image pickup unit 1 as the optical unit provided on the distal end portion 110 will be described.

Hereinafter, a direction (a left side in each figure) from the image pickup unit 1 to an object along a photographing optical axis O of an object image may be called a distal end, a front part or an object side, and the opposite direction may be called a proximal end, a rear part or an image side.

The image pickup unit 1 which is the optical unit of the present embodiment includes a lens unit 10 and an image pickup device unit 20 in an order from the object side to be the front part as illustrated in FIG. 2.

The lens unit 10 includes a cylindrical lens holding frame 11 as a lens frame, and a group 13 of a plurality of objective lenses as an objective optical system held by the lens holding frame 11.

The image pickup device unit 20 includes a cylindrical image pickup device holding frame 12 as a device frame, an optical member 14 and cover glass 22 such as a transparent glass plate, and an image pickup device 21.

To the optical member 14 of the image pickup device unit 20, the cover glass 22 as a transparent cover body that protects a light receiving section 21a of the image pickup device 21 is stuck by an optical adhesive or the like. Then, the optical member 14 is fitted and fixed to the image pickup device holding frame 12. That is, for the image pickup device unit 20, the image pickup device holding frame 12 on the distal end side holds the image pickup device 21 on the proximal end side through the optical member 14 and the cover glass 22.

For the image pickup device 21, an image pickup substrate section mounted with the light receiving section 21a in a rectangular shape here is connected with the electric cable 115 through an electronic substrate section 24 such as an FPC. Note that, on the electronic substrate section 24, a plurality of electronic components 25 are mounted.

The image pickup device 21 is the one for which a plurality of devices that output electric signals according to the light indicated by the photographing optical axis O to be made incident at predetermined timing are arrayed at a planar light receiving section, and for example, various kinds of forms such as a form generally called a CCD (charge-coupled device), or a CMOS (complementary metal oxide semiconductor) sensor are applied.

In addition, an outer circumference of a fitting section of the lens holding frame 11 of the lens unit 10 and an inner circumference of a fitting section of the image pickup device holding frame 12 of the image pickup device unit 20 are fitted and fixed.

Thus, the image pickup device 21 is disposed such that the above-described light receiving section 21a is positioned on an image forming surface of the objective lens group 13 of the lens unit 10.

Note that the image pickup unit 1 is provided with a heat-shrinkable tube 15 which is fixed to an outer frame portion of the image pickup device holding frame 12 at a distal end portion to form an exterior and is for keeping watertightness of the inside.

Then, for the image pickup unit 1, a filler 26 such as an adhesive that covers the image pickup device 21, the electronic substrate section 24 and the like is filled inside the heat-shrinkable tube 15 and the watertightness of the inside is kept.

Here, fitting and fixation of the lens unit 10 and the image pickup device unit 20 in the image pickup unit 1 as the optical unit of the present embodiment will be described below in detail.

As illustrated in FIG. 2 and FIG. 3, in the image pickup unit 1, the fitting section of the lens holding frame 11 of the lens unit 10 is fitted to be interpolated to the fitting section of the image pickup device holding frame 12 of the image pickup device unit 20. At the time, fitting is performed such that centers of the outer circumference of the fitting section of the lens holding frame 11 and the inner circumference of the fitting section of the image pickup device holding frame 12 coincide.

Note that the centers of the outer circumference of the fitting section of the lens holding frame 11 and the inner circumference of the fitting section of the image pickup device holding frame 12 coincide with the photographing optical axis O of the object image passing through the objective lens group 13 held by the lens holding frame 11.

Then, the fitting sections of the lens holding frame 11 and the image pickup device holding frame 12 are bonded by a welding section 30 at one location here in the state of being fitted to each other, and fixed in the state that a bonding material 31 such as an adhesive is filled so as to fill a minute gap of a mutually overlapping part and airtightness (watertightness) is kept.

When describing the manufacture process, for the lens unit 10 and the image pickup device unit 20, as illustrated in FIG. 4, from the state of being separated from each other, the lens holding frame 11 is fitted and inserted to the inside of the image pickup device holding frame 12.

At the time, the lens holding frame 11 is moved to the front and rear of the object side and the image side along a longitudinal direction along the photographing optical axis O regarding the image pickup device holding frame 12, and a predetermined fitting position to the image pickup device holding frame 12 is adjusted to be a predetermined position at which the image forming surface of the light of the photographing optical axis O by the objective lens group 13 coincides with the light receiving section 21a of the image pickup device 21 held by the image pickup device holding frame 12.

That is, for the lens unit 10 and the image pickup device unit 20, the predetermined fitting position in the longitudinal direction of the lens holding frame 11 and the image pickup device holding frame 12 is adjusted so as to be a focusing position at which the object image converged by the objective lens group 13 detected by a device group arrayed at the light receiving section 21a of the image pickup device 21 is turned to a predetermined optical performance, so called a position at which a focused object image is obtained.

Then, the lens unit 10 and the image pickup device unit 20 are fixed with a jig or the like not shown in the figure so that the fitting position of the fitting sections of the lens holding frame 11 and the image pickup device holding frame 12 is not shifted, and for example, at an outer circumference middle section of the image pickup device holding frame 12 on an outer side, as illustrated in FIG. 5, the welding section 30 mutually welded by laser welding by irradiation of a laser beam for example is formed, and the lens holding frame 11 and the image pickup device holding frame 12 are immovably fixed.

Next, for the lens unit 10 and the image pickup device unit 20, as illustrated in FIG. 6, the bonding material 31 which is a thermosetting type adhesive for example is filled so as to fill a minute gap generated at the fitting sections of the lens holding frame 11 and the image pickup device holding frame 12. Note that the bonding material 31 is applied along an end face on the object side of the fitting section of the image pickup device holding frame 12, thereby infiltrating into the minute gap by a so-called capillary phenomenon.

Then, for the lens unit 10 and the image pickup device unit 20, thermosetting treatment of hardening the bonding material 31 filled in the gap of the fitting sections of the lens holding frame 11 and the image pickup device holding frame 12 is performed.

In this way, the image pickup unit 1 is configured such that the fitting position of the lens holding frame 11 of the lens unit 10 and the image pickup device holding frame 12 of the image pickup device unit 20 is fixed by the welding section 30, and airtightly (watertightly) fixed by the bonding material 31 filled and hardened in the overlapping gap of the lens holding frame 11 and the image pickup device holding frame 12.

That is, the image pickup unit 1 is configured such that the lens unit 10 and the image pickup device unit 20 are strongly fixed at a position of satisfying the predetermined optical performance at which the focus position of the objective lens group 13 and the light receiving section 21a of the image pickup device 21 coincide by the welding section 30, and are airtightly (watertightly) bonded by the bonding material 31.

For the image pickup unit 1 configured as described above, during manufacture, when executing the thermosetting treatment to the bonding material 31 that airtightly (watertightly) bonds the lens unit 10 and the image pickup device unit 20, and when executing high temperature and high pressure sterilization treatment (autoclave treatment) to the endoscope 101, even if the bonding material 31, the lens holding frame 11 and the image pickup device holding frame 12 are expanded, contracted or the like, since the lens holding frame 11 and the image pickup device holding frame 12 are strongly fixed by the welding section 30, the shift of the lens unit 10 and the image pickup device unit 20 is prevented.

Therefore, the image pickup unit 1 can maintain a state that the predetermined fitting position of the lens unit 10 and the image pickup device unit 20 is fixed without being shifted even under a high temperature environment such as a time period of manufacture and a time period of high temperature and high pressure sterilization disinfecting, satisfy conformance quality of the predetermined optical performance and also prevent degradation of the optical performance.

Note that, for the welding section 30 that fixes the lens holding frame 11 of the lens unit 10 and the image pickup device holding frame 12 of the image pickup device unit 20 so as not to shift, without being limited to laser welding, various kinds of welding methods such as ultrasound welding or spot welding may be applied.

Further, for the image pickup unit 1, it is preferable to form the welding section 30 for fixing the lens holding frame 11 and the image pickup device holding frame 12 at a position of a low image height of the light receiving section 21a of the image pickup device 21, that is, since the light receiving section 21a is a rectangular shape here, on an extension line of a position facing a center of one of sides of the light receiving section 21a.

It is because there is a possibility that the objective lens group 13 provided in the lens holding frame 11 is deformed or the like by heat, a pressure or the like generated when the welding section 30 is formed and a refractive index of light is influenced, and the endoscope image is sometimes distorted due to the influence.

That is, for the image pickup unit 1, when the welding section 30 is formed at a position of a high image height of the light receiving section 21a, on an extension line in a diagonal direction of the light receiving section 21a in the rectangular shape here, in the case that a part of the objective lens group 13 which is close to and faces the welding section 30 is deformed during welding of forming the welding section 30, there is a possibility that the object image distorted by refraction of light at the deformed part is formed at the light receiving section 21a.

Therefore, for the image pickup unit 1, by forming the welding section 30 for fixing the lens holding frame 11 and the image pickup device holding frame 12 on the extension line facing the position of the low image height of the light receiving section 21a of the image pickup device 21, even when the objective lens group 13 at the part is deformed or the like, the influence of the distortion of the object image in a range formed at the light receiving section 21a can be reduced as much as possible.

Further, for the image pickup unit 1, during the manufacture, after applying the bonding material 31 beforehand to a proximal end outer circumferential section of the fitting section of the lens holding frame 11 of the lens unit 10 or a distal end inner circumferential section of the fitting section of the image pickup device holding frame 12 of the image pickup device unit 20, the lens holding frame 11 and the image pickup device unit 20 may be fitted, the welding section 30 may be formed, and the thermosetting treatment of the bonding material 31 may be executed lastly.

Modifications

Note that the image pickup unit 1 may be the configuration of various modifications described below.

First Modification

In the image pickup unit 1 of the present modification, as illustrated in FIG. 7, two welding sections 30a and 30b formed by the welding at the fitting section of the lens holding frame 11 of the lens unit 10 and the fitting section of the image pickup device holding frame 12 of the image pickup device unit 20 are formed at positions point-symmetrical about a center (a point that the photographing optical axis O passes through) of the fitting section of the lens holding frame 11 and the image pickup device holding frame 12.

Again, for the image pickup unit 1, the two welding sections 30a and 30b for fixing the lens holding frame 11 and the image pickup device holding frame 12 are formed at positions on the extension line facing the position of the low image height of the light receiving section 21a of the image pickup device 21.

Note that, for the lens unit 10 and the image pickup device unit 20, by simultaneously forming the two welding sections 30a and 30b, the lens holding frame 11 and the image pickup device holding frame 12 can be fixed without the shift of an outer diameter center of the fitting section of the lens holding frame 11 and an inner diameter center of the fitting section of the image pickup device holding frame 12.

In the image pickup unit 1 configured in such a way, by forming the two welding sections 30a and 30b, the lens unit 10 and the image pickup device unit 20 are turned to the configuration of being more strongly fixed at the position of satisfying the predetermined optical performance at which the focus position of the objective lens group 13 and the light receiving section 21a of the image pickup device 21 coincide.

Second Modification

In the image pickup unit 1 of the present modification, as illustrated in FIG. 8, four welding sections 30a to 30d for fixing the lens holding frame 11 and the image pickup device holding frame 12 are formed at equal intervals around the center of the fitting section of the lens holding frame 11 and the image pickup device holding frame 12.

Note that the two welding sections 30a and 30b are, similarly to the first modification, formed at positions point-symmetrical about the center of the fitting section of the lens holding frame 11 and the image pickup device holding frame 12.

In addition, the two welding sections 30c and 30d are formed at positions of being rotated by 90 degrees around the center of the fitting section of the lens holding frame 11 and the image pickup device holding frame 12 from the other two welding sections 30a and 30b, which are the positions point-symmetrical to the center of the fitting section of the lens holding frame 11 and the image pickup device holding frame 12.

Then, for the four welding sections 30a to 30d, the two welding sections 30 for fixing the lens holding frame 11 and the image pickup device holding frame 12 are again formed at the positions on the extension line facing the position of the low image height of the light receiving section 21a of the image pickup device 21.

In the image pickup unit 1 configured in such a way, by forming the four welding sections 30a to 30d, the lens unit 10 and the image pickup device unit 20 are turned to the configuration of being further strongly fixed at the position of satisfying the predetermined optical performance at which the focus position of the objective lens group 13 and the light receiving section 21a of the image pickup device 21 coincide.

Third Modification

In the image pickup unit 1 of the present modification, as illustrated in FIG. 9, the lens holding frame 11 and the image pickup device holding frame 12 may be fixed by a plurality, 12 pieces here, of welding sections 30a to 30j.

It is preferable that the plurality of welding sections 30a to 30j include an even number of welding sections formed at equal intervals around the center of the fitting section of the lens holding frame 11 and the image pickup device holding frame 12.

Note that the welding sections 30a to 30j are formed such that two of the welding sections are paired and oppositely arranged at the positions point-symmetrical about the center of the fitting section of the lens holding frame 11 and the image pickup device holding frame 12.

Fourth Modification

In the image pickup unit 1 of the present modification, as illustrated in FIG. 10, the welding section 30 that fixes the lens holding frame 11 and the image pickup device holding frame 12 is formed at an edge section at a part of a distal end face of the image pickup device holding frame 12 at the distal end of the fitting section of the image pickup device holding frame 12.

In the image pickup unit 1 configured in such a way, since the welding section 30 is not formed at a middle part of the fitting section of the image pickup device holding frame 12 of the welding section 30, the bonding material 31 is easily and uniformly filled in a gap of a part where the lens holding frame 11 and the image pickup device holding frame 12 overlap, and the lens unit 10 and the image pickup device unit 20 can be airtightly (watertightly) bonded more surely.

Reference Example

The image pickup unit 1 may be the configuration of various reference examples described below, other than the individual modifications described above.

First Reference Example

As illustrated in FIG. 11, the image pickup unit 1 may be configured such that the bonding material 31 that airtightly (watertightly) bonds the lens unit 10 and the image pickup device unit 20 is applied and hardened at the edge section at a part of the distal end face of the fitting section of the image pickup device holding frame 12.

Second Reference Example

As illustrated in FIG. 12, the image pickup unit 1 may be configured such that a recessed circumferential groove 12a that functions as a bonding material reservoir (adhesion reservoir) where an excessive adhesive or the like as the bonding material 31 that airtightly (watertightly) bonds the lens unit 10 and the image pickup device unit 20 flows into is formed at the inner circumferential section of the image pickup device holding frame 12.

Note that the circumferential groove 12a is provided in the inner circumferential section more on the proximal end side than the fitting section of the image pickup device holding frame 12 in the present reference example, but it is not exclusive and the circumferential groove 12a may be formed at the inner circumferential section of the fitting section of the image pickup device holding frame 12.

Third Reference Example

As illustrated in FIG. 13, the image pickup unit 1 may be configured such that a recessed circumferential groove 11a that functions as a bonding material reservoir (adhesion reservoir) where an excessive adhesive or the like as the bonding material 31 that airtightly (watertightly) bonds the lens unit 10 and the image pickup device unit 20 flows into is formed at the outer circumferential section of the lens holding frame 11.

Note that the circumferential groove 11a is provided in the outer circumferential section of the fitting section of the lens holding frame 11, but it is not exclusive and the circumferential groove 11a may be formed at the outer circumferential section more on the proximal end side than the fitting section of the lens holding frame 11.

Fourth Reference Example

As illustrated in FIG. 14, the image pickup unit 1 may be configured such that the airtightness (watertightness) is improved more by forming the distal end of the image pickup device frame more on the distal end side than the fitting section of the image pickup device holding frame 12 of the image pickup device unit 20 into a tapered surface 12b and filling the bonding material 31 that airtightly (watertightly) bonds the lens unit 10 and the image pickup device unit 20 also to the distal end part of the image pickup device holding frame 12 formed by the tapered surface 12b to cover the entire circumference of the distal end of the image pickup device unit 20. Further, by turning the distal end face of the image pickup device holding frame 12 into the tapered surface 12b, work of filling the bonding material 31 becomes easy to perform.

Fifth Reference Example

As illustrated in FIG. 15, the image pickup unit 1 may be configured such that the airtightness (watertightness) is improved more by providing a flange section 11b more on the distal end side than the fitting section of the lens holding frame 11 of the lens unit 10, forming the proximal end face of the flange section 11b into a tapered surface 11c and filling the bonding material 31 that airtightly (watertightly) bonds the lens unit 10 and the image pickup device unit 20 also between the tapered surface 12b and the distal end face of the image pickup device holding frame 12 to cover the entire circumference of the distal end of the image pickup device unit 20. Again, by turning the proximal end face of the flange section 11b of the lens holding frame 11 into the tapered surface 11c, the work of filling the bonding material 31 becomes easy to perform.

Second Embodiment

Next, an optical unit and an endoscope of the second embodiment of the present invention will be described below based on the drawings.

Note that, in the following description, same signs are used for same components described in the first embodiment described above, and detailed descriptions of the components are omitted.

Figure 16:
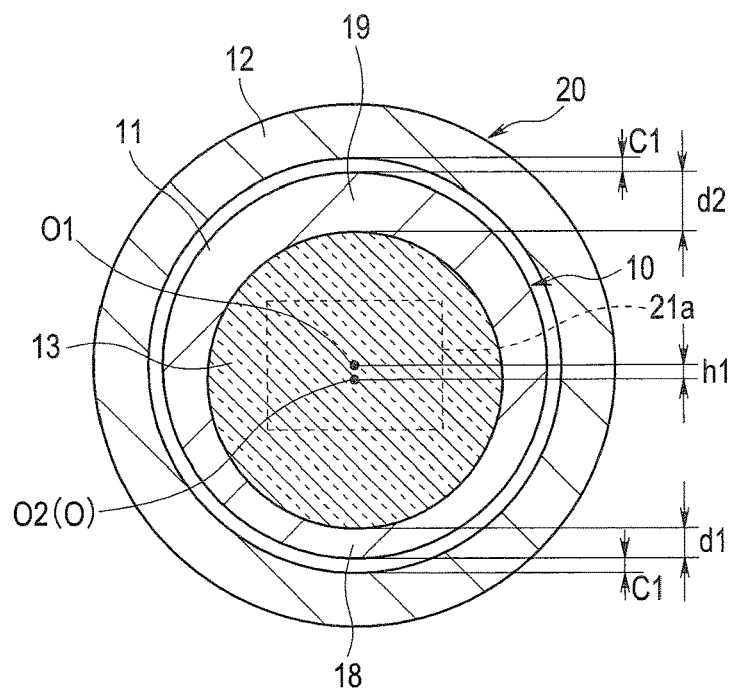
FIG. 16 is a horizontal sectional view illustrating a configuration of an optical unit in a state that a lens unit and an image pickup device unit are fitted relating to a second embodiment.
Figure 17:
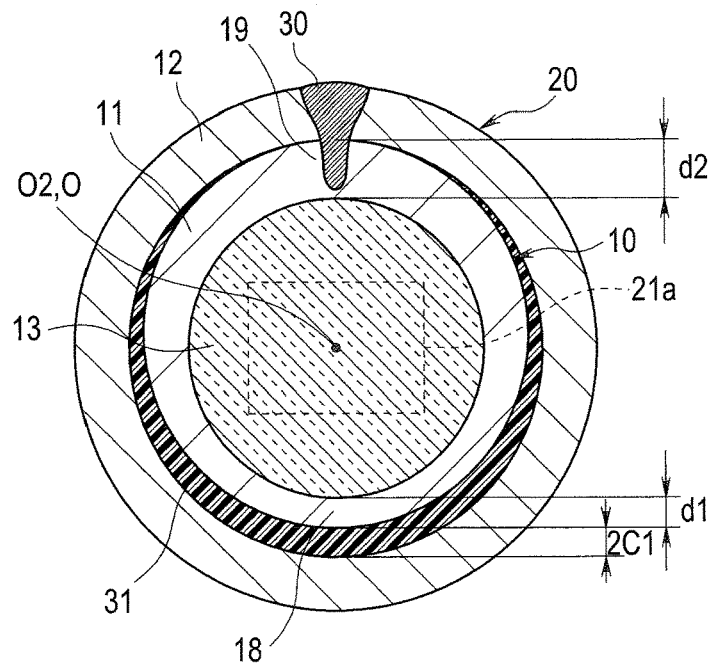
FIG. 17 is a horizontal sectional view illustrating a configuration of the optical unit in a state that the lens unit and the image pickup device unit are fitted and fixed relating to the second embodiment.
Figure 18:
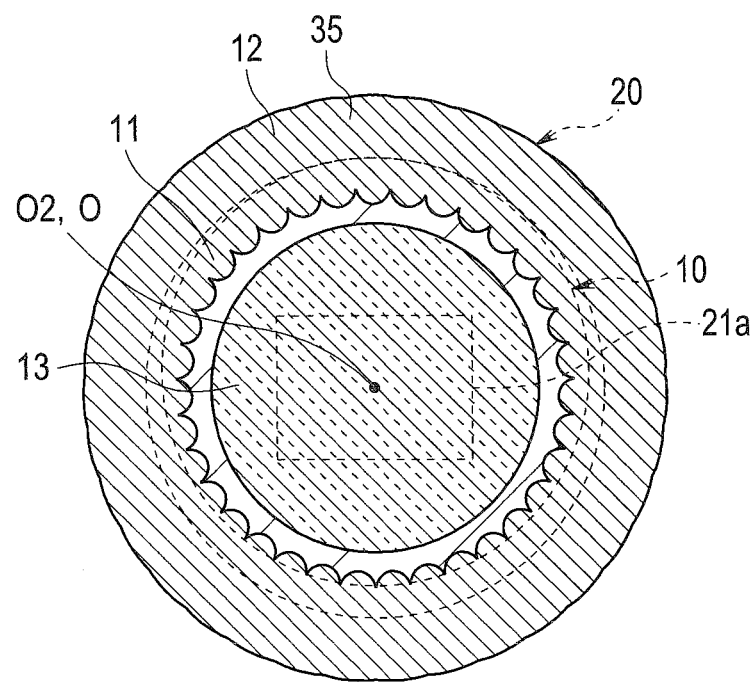
FIG. 18 is a horizontal sectional view illustrating a configuration of the optical unit in the state that the lens unit and the image pickup device unit are fitted and fixed in a first modification relating to the second embodiment.
Figure 20:
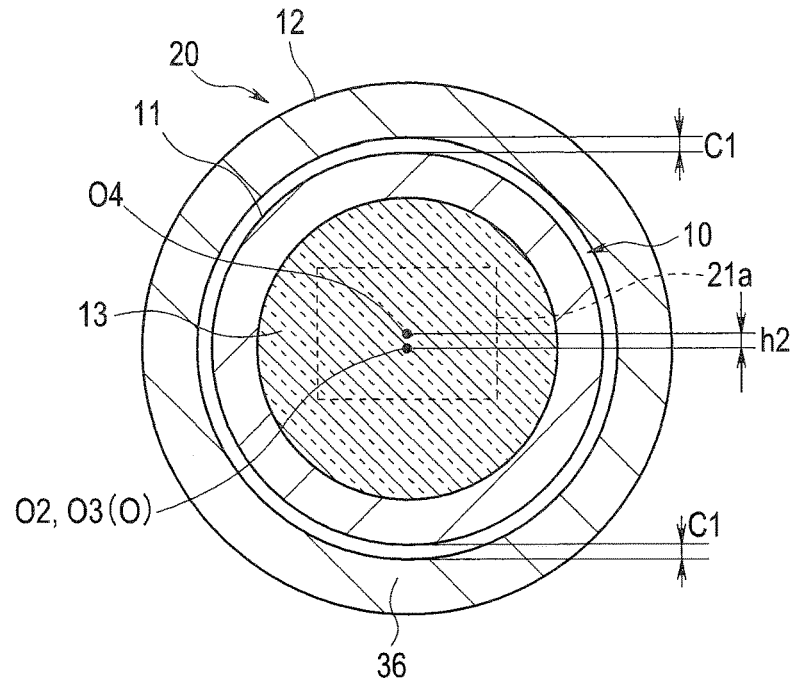
FIG. 20 is a horizontal sectional view illustrating a configuration of the optical unit in the state that the lens unit and the image pickup device unit are fitted relating to the second embodiment.
Figure 21:
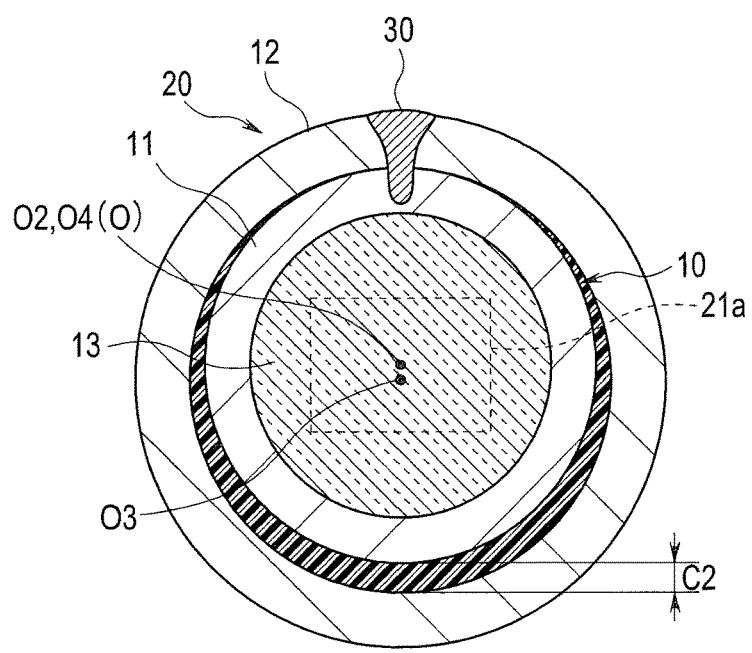
FIG. 21 is a horizontal sectional view illustrating a configuration of the optical unit in the state that the lens unit and the image pickup device unit are fitted and fixed relating to the second embodiment.
Figure 22:
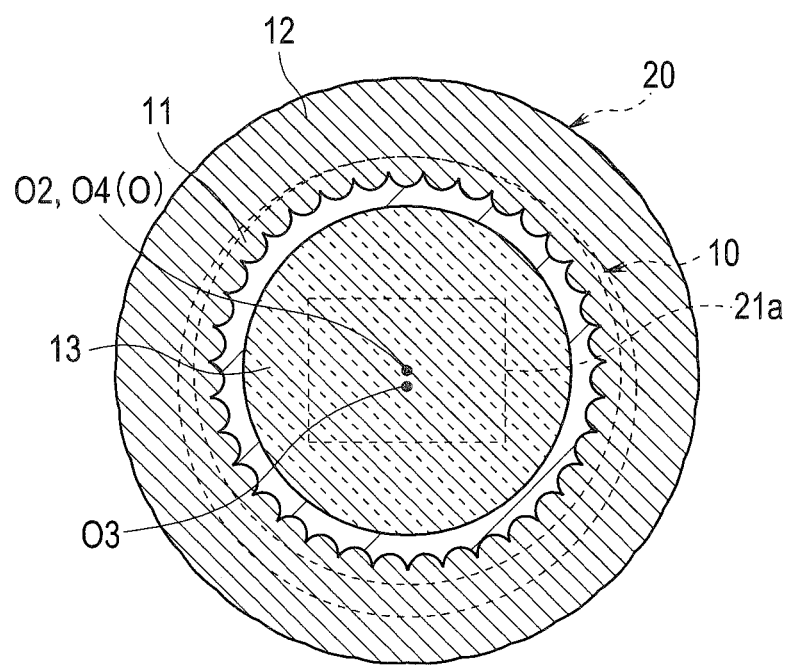
FIG. 22 is a horizontal sectional view illustrating a configuration of the optical unit in the state that the lens unit and the image pickup device unit are fitted and fixed in a third modification relating to the second embodiment.

In addition, FIG. 16 is a horizontal sectional view illustrating a configuration of the optical unit in the state that the lens unit and the image pickup device unit are fitted, FIG. 17 is a horizontal sectional view illustrating a configuration of the optical unit in the state that the lens unit and the image pickup device unit are fitted and fixed, FIG. 18 is a horizontal sectional view illustrating a configuration of the optical unit in the state that the lens unit and the image pickup device unit are fitted and fixed in a first modification, FIG. 19 is a sectional view illustrating a state before the lens unit and the image pickup device unit are fitted in a second modification, FIG. 20 is a horizontal sectional view illustrating a configuration of the optical unit in the state that the lens unit and the image pickup device unit are fitted, FIG. 21 is a horizontal sectional view illustrating a configuration of the optical unit in the state that the lens unit and the image pickup device unit are fitted and fixed, and FIG. 22 is a horizontal sectional view illustrating a configuration of the optical unit in the state that the lens unit and the image pickup device unit are fitted and fixed in a third modification.

Now, for the image pickup unit 1, when forming the welding section 30 by fitting the lens holding frame 11 of the lens unit 10 and the image pickup device holding frame 12 of the image pickup device unit 20, a very small gap is sometimes generated at the fitting section of the lens holding frame 11 and the image pickup device holding frame 12, and since the welding section 30 is contracted during coagulation, the outer diameter center of the fitting section of the lens holding frame 11 of the lens unit 10 and the inner diameter center of the fitting section of the image pickup device holding frame 12 of the image pickup device unit 20 become eccentric and shifted, and the lens unit 10 is sometimes shifted from a predetermined position and fixed to the image pickup device unit 20 in a direction orthogonal to the photographing optical axis O.

In such a manner, when the fitting section of the lens holding frame 11 of the lens unit 10 becomes eccentric to the fitting section of the image pickup device holding frame 12 of the image pickup device unit 20, the center of the objective lens group 13 held by the lens holding frame 11 of the lens unit 10 is shifted from the predetermined position regarding the image pickup device unit 20 in the direction orthogonal to the photographing optical axis O. Thus, the photographing optical axis O of the object image is shifted from a predetermined image forming center position of the light receiving section 21a of the image pickup device 21 provided on the image pickup device holding frame 12 of the image pickup device unit 20, the center of the light receiving section 21a in this case, and there is a risk that the conformance quality of the predetermined optical performance cannot be obtained.

Then, the image pickup unit 1 of the present embodiment is configured such that, as illustrated in FIG. 16, an outer diameter center O1 of the fitting section of the cylindrical lens holding frame 11 of the lens unit 10 and an inner diameter center O2 of a lens holding hole holding the objective lens group 13 of the lens holding frame 11 are shifted by a predetermined distance h1. Note that the inner diameter center O2 of the lens holding frame 11 coincides with the center of the held objective lens group 13, that is, the photographing optical axis O of the object image.

Therefore, the lens holding frame 11 is configured such that an inner circumferential surface of the lens holding hole is shifted by the predetermined distance h1 regarding an outer circumferential surface of the fitting section and the respective centers are eccentric. That is, the lens unit 10 is configured such that the inner diameter center O2 of the lens holding hole holding the objective lens group 13 of the lens holding frame 11 is eccentric in a predetermined direction by the predetermined distance h1 regarding the outer diameter center O1 of the fitting section of the lens holding frame 11.

Therefore, the lens holding frame 11 becomes a minimum thickness section 18 having a predetermined thickness d1, and a position point-symmetrical to the minimum thickness section 18 is a maximum thickness section 19 having a predetermined thickness d2 thicker than the predetermined thickness d1 (d1<d2).

Note that the predetermined distance h1 is set at a distance (h1≈C1) almost same as a clearance C1 as a minute gap formed in a circumferential direction between the outer circumferential surface of the fitting section of the lens holding frame 11 and the inner circumferential surface of the fitting section of the image pickup device holding frame 12 in the state that the lens unit 10 is inserted and fitted to the image pickup device unit 20.

For the image pickup unit 1 configured as above, after the lens unit 10 is inserted and fitted to the image pickup device unit 20, as illustrated in FIG. 17, the welding section 30 is formed at the outer circumference middle section of the fitting section of the image pickup device holding frame 12 to be a side of the maximum thickness section 19 of the fitting section of the lens holding frame 11, and the lens holding frame 11 and the image pickup device holding frame 12 are immovably fixed.

At the time, in a process of forming the welding section 30, the welding section 30 is contracted during the coagulation, the maximum thickness section 19 of the fitting section of the lens holding frame 11 is drawn in a direction of an inner circumferential surface side of the fitting section of the image pickup device holding frame 12, that is, an opposite side of the eccentric direction of the inner diameter center O2 of the lens holding hole regarding the outer diameter center O1 of the fitting section, the outer circumferential surface of the maximum thickness section 19 and the inner circumferential surface of the fitting section of the image pickup device holding frame 12 are turned to an abutted state, and the lens holding frame 11 is fixed to the image pickup device holding frame 12 by the welding section 30.

Then, the bonding material 31 is filled so as to fill the gap generated at the fitting section of the lens holding frame 11 and the image pickup device holding frame 12, the thermosetting treatment is executed, and the lens unit 10 and the image pickup device unit 20 are airtightly (watertightly) fixed.

In this way, the lens unit 10 and the image pickup device unit 20 are bonded in the state that the inner diameter center O2 of the lens holding hole of the lens holding frame 11 coincides with the inner diameter center of the fitting section of the image pickup device holding frame 12 in a bonded state.

Thus, the image pickup unit 1 is configured such that, since the center of the objective lens group 13 held by the lens holding frame 11 coincides with the inner diameter center of the fitting section of the image pickup device holding frame 12, the photographing optical axis O of the object image is made incident on the predetermined image forming center position of the light receiving section 21a of the image pickup device 21 held by the image pickup device holding frame 12, the center of the light receiving section 21a in this case.

Note that the predetermined thickness d2 of the maximum thickness section 19 is a sum of the predetermined thickness d1 of the minimum thickness section 18 and double of the clearance C1 (d2=d1+2C1).

As described above, the image pickup unit 1 is configured to satisfy the conformance quality of the predetermined optical performance by attaining the configuration that the outer diameter center O1 of the fitting section of the lens holding frame 11 and the inner diameter center O2 of the lens holding hole are shifted and made eccentric beforehand so that the photographing optical axis O of the object image is made incident on the predetermined image forming center position of the light receiving section 21a of the image pickup device 21, the center of the light receiving section 21a in this case, on the assumption that the lens unit 10 is moved in a direction of forming the welding section 30 when the lens unit 10 and the image pickup device unit 20 are to be fixed by the welding section 30.

Note that the lens unit 10 may be provided with an index section for easily identifying a position to form the welding section 30, that is, a position of the maximum thickness section 19 of the fitting section of the lens holding frame 11, from an outer circumferential section side of the fitting section of the image pickup device holding frame 12 of the image pickup device unit 20. The index section may be formed by partial surface treatment of providing a notch, a planar section or a marker by plating, vapor deposition, coating or the like, for example, indicating the position of the maximum thickness section 19 on a position not overlapping with the image pickup device holding frame 12 of the lens holding frame 11.

First Modification

For the image pickup unit 1 of the present modification, as illustrated in FIG. 18, after the lens unit 10 is inserted and fitted to the image pickup device unit 20, the above-described welding section 30 (without a sign in FIG. 18) may be forming at the outer circumference middle section of the fitting section of the image pickup device holding frame 12 to be the side of the maximum thickness section 19 of the fitting section of the lens holding frame 11 first, and thereafter, a welding section 35 where the entire outer circumference of the fitting section of the image pickup device holding frame 12 is continuously welded may be formed.

Note that, since the outer circumference middle section of the fitting section of the image pickup device holding frame 12 on the side of the maximum thickness section 19 of the fitting section of the lens holding frame 11 is fixed by the welding section 30 first, even when the welding section 35 is formed by continuously welding the entire outer circumference of the fitting section of the image pickup device holding frame 12 thereafter, the lens unit 10 and the image pickup device unit 20 are not shifted, and the lens unit 10 and the image pickup device unit 20 are fixed in the state that the inner diameter center O2 of the lens holding hole of the lens holding frame 11 coincides with the inner diameter center of the fitting section of the image pickup device holding frame 12.

In the image pickup unit 1 configured in such a way, in addition to the above-described effects, since the gap formed between the lens unit 10 and the image pickup device unit 20 is filled by the welding section 35, the lens unit 10 and the image pickup device unit 20 are airtightly (watertightly) fixed without providing the bonding material 31 in the gap.

Second Modification

The image pickup unit 1 of the present modification is configured, as illustrated in FIG. 19, such that a center O3 of a cylindrical section of the image pickup device holding frame 12 and a center O4 of the light receiving section 21a of the image pickup device 21 are shifted by a predetermined distance h2.

Note that the predetermined distance h2 is set at a distance (h2≈C1) almost the same as the clearance C1 as the minute gap formed in the circumferential direction between the outer circumferential surface of the lens holding frame 11 and the inner circumferential surface of the cylindrical section of the image pickup device holding frame 12 in the state that the lens unit 10 is inserted and fitted to the image pickup device unit 20.

For the image pickup unit 1 configured as above, as illustrated in FIG. 20, after the lens unit 10 is inserted and fitted to the image pickup device unit 20, as illustrated in FIG. 21, the welding section 30 is formed, and the lens holding frame 11 and the image pickup device holding frame 12 are immovably fixed.

At the time, in the process of forming the welding section 30, the welding section 30 is contracted during the coagulation, and the lens holding frame 11 is drawn to the inner circumferential surface side of the cylindrical section of the image pickup device holding frame 12, is turned to the state that the outer circumferential surface and the inner circumferential surface of the cylindrical section of the image pickup device holding frame 12 are abutted, and is fixed to the image pickup device holding frame 12 by the welding section 30.

Then, the bonding material 31 is filled so as to fill the gap generated at the overlapping part of the cylindrical section of the lens holding frame 11 and the image pickup device holding frame 12, the thermosetting treatment is executed, and the lens unit 10 and the image pickup device unit 20 are airtightly (watertightly) fixed.

In this way, the lens unit 10 and the image pickup device unit 20 are bonded in the state that the inner diameter center O2 of the lens holding frame 11 coincides with the center O4 of the light receiving section 21a of the image pickup device 21 in a bonded state.

As described above, the image pickup unit 1 is configured to satisfy the conformance quality of the predetermined optical performance by attaining the configuration that the center O3 of the cylindrical section of the image pickup device holding frame 12 and the center O4 of the light receiving section 21a of the image pickup device 21 are shifted and made eccentric beforehand so that the photographing optical axis O of the object image is made incident on the center of the light receiving section 21a of the image pickup device 21, on the assumption that the lens unit 10 is moved in the direction of forming the welding section 30 when the lens unit 10 and the image pickup device unit 20 are to be fixed by the welding section 30.

Note that the lens unit 10 may be provided with the index section for easily identifying the position to form the welding section 30 from the outer circumferential section side of the cylindrical section of the image pickup device holding frame 12 of the image pickup device unit 20. The index section may be formed by the partial surface treatment of providing a notch, a planar section or a marker by plating, vapor deposition, coating or the like, for example, indicating the position of the eccentric direction of the light receiving section 21a of the image pickup device 21 on the outer circumferential section of the image pickup device holding frame 12.

Third Modification

For the image pickup unit 1 of the present modification, as illustrated in FIG. 22, after the lens unit 10 is inserted and fitted to the image pickup device unit 20, the above-described welding section 30 may be formed at the outer circumference middle section of the cylindrical section of the image pickup device holding frame 12 first, and thereafter, the welding section 35 where the entire outer circumference of the cylindrical section of the image pickup device holding frame 12 is continuously welded may be formed.

Note that, since the outer circumference middle section of the cylindrical section of the image pickup device holding frame 12 is fixed by the welding section 30, even when the welding section 35 is formed by continuously welding the entire outer circumference of the cylindrical section of the image pickup device holding frame 12 thereafter, the lens unit 10 and the image pickup device unit 20 are not shifted, and the lens unit 10 and the image pickup device unit 20 are fixed in the state that the inner diameter center O2 of the lens holding frame 11 coincides with the center of the image pickup device holding frame 12.

In the image pickup unit 1 configured in such a way, in addition to the above-described effects, since the gap formed between the lens unit 10 and the image pickup device unit 20 is filled by the welding section 35, the lens unit 10 and the image pickup device unit 20 are airtightly (watertightly) fixed without providing the bonding material 31 in the gap.

Third Embodiment

Next, an optical unit and an endoscope of the third embodiment of the present invention will be described below based on the drawings.

Note that, in the following description, the same signs are used for the same components described in the first embodiment and the second embodiment described above, and the detailed descriptions of the components are omitted.

Figure 23:
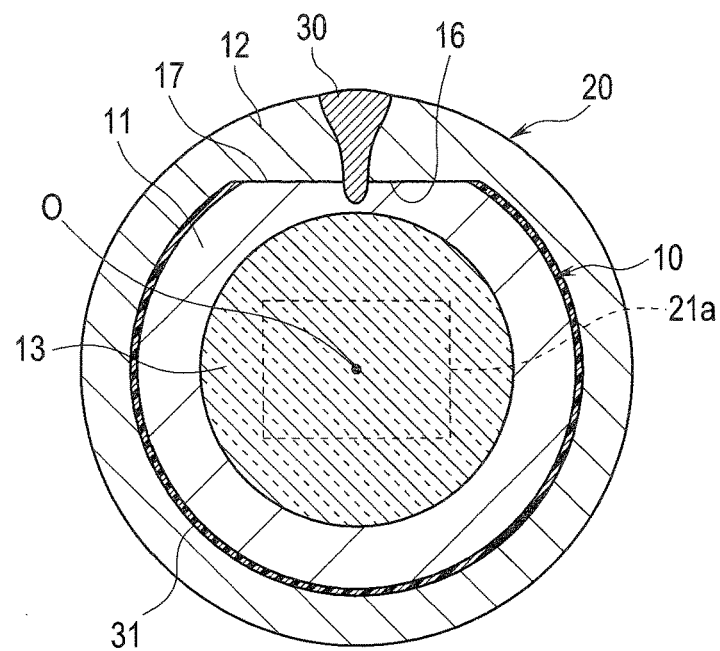
FIG. 23 is a horizontal sectional view illustrating a configuration of an optical unit in a state that a lens unit and an image pickup device unit are fitted and fixed relating to a third embodiment.
Figure 24:
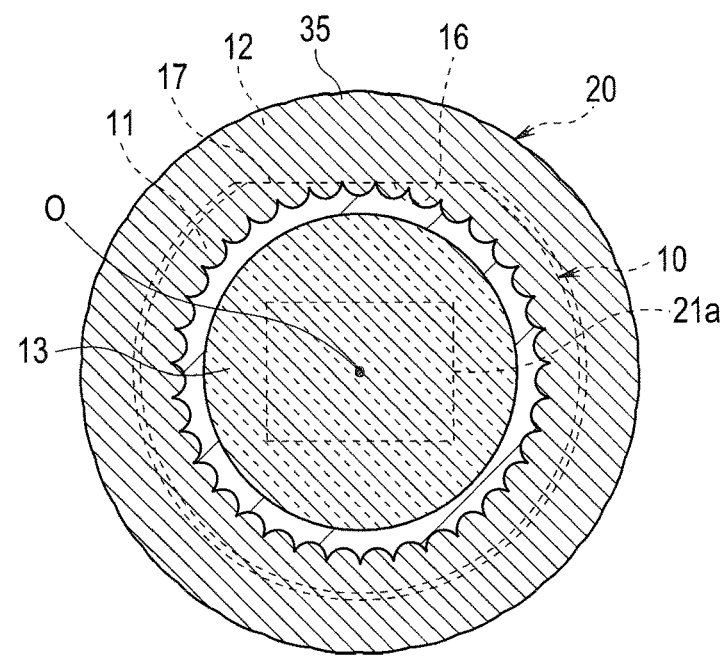
FIG. 24 is a horizontal sectional view illustrating a configuration of the optical unit in the state that the lens unit and the image pickup device unit are fitted and fixed in a modification relating to the third embodiment.

In addition, FIG. 23 is a horizontal sectional view illustrating a configuration of the optical unit in the state that the lens unit and the image pickup device unit are fitted and fixed, and FIG. 24 is a horizontal sectional view illustrating a configuration of the optical unit in the state that the lens unit and the image pickup device unit are fitted and fixed in a modification.

For the image pickup unit 1 of the present embodiment, as illustrated in FIG. 23, a planar section 16 is formed at a part of the outer circumference of the fitting section of the lens holding frame 11 of the lens unit 10, and a planar section 17 to be abutted to the planar section 16 and brought into surface contact is formed at a part of the inner circumference of the fitting section of the image pickup device holding frame 12 of the image pickup device unit 20.

Then, in the state that the planar section 16 of the lens holding frame 11 and the planar section 17 of the image pickup device holding frame 12 are abutted and brought into surface contact, the state is such that the outer diameter center of the fitting section of the lens holding frame 11 and the inner diameter center of the fitting section of the image pickup device holding frame 12 coincide.

In addition, for the image pickup unit 1, the welding section 30 is formed at a part where the planar section 16 of the lens holding frame 11 and the planar section 17 of the image pickup device holding frame 12 are abutted and brought into surface contact, and the lens holding frame 11 and the image pickup device holding frame 12 are immovably fixed, and airtightly (watertightly) fixed by filling the bonding material 31 so as to fill the gap generated at the fitting section of the lens holding frame 11 and the image pickup device holding frame 12 and executing the thermosetting treatment.

In the image pickup unit 1 configured as above, when forming the welding section 30 at the part where the planar sections 16 and 17 formed at the respective fitting sections of the lens holding frame 11 of the lens unit 10 and the image pickup device holding frame 12 of the image pickup device unit 20 are abutted and brought into surface contact, even when the welding section 30 is contracted during the coagulation, the lens unit 10 is not moved regarding the image pickup device unit 20 and is thus fixed without shifting from the state that the outer diameter center of the fitting section of the lens holding frame 11 coincides with the inner diameter center of the fitting section of the image pickup device holding frame 12.

Thus, since the center of the objective lens group 13 held by the lens holding frame 11 also coincides with the inner diameter center of the fitting section of the image pickup device holding frame 12, the image pickup unit 1 is configured such that the photographing optical axis O of the object image is made incident on the predetermined image forming center position of the light receiving section 21a of the image pickup device 21 held by the image pickup device holding frame 12, the center of the light receiving section 21a in this case.

Modification

For the image pickup unit 1 of the present modification, as illustrated in FIG. 24, the above-described welding section 30 (no sign in FIG. 24) may be formed at the part where the planar section 16 of the lens holding frame 11 and the planar section 17 of the image pickup device holding frame 12 are abutted and brought into surface contact first, and thereafter, the welding section 35 where the entire outer circumference of the fitting section of the image pickup device holding frame 12 is continuously welded may be formed.

In the image pickup unit 1 configured in such a way, in addition to the above-described effects, similarly to the modification of the second embodiment, since the gap formed between the fitting sections of the lens unit 10 and the image pickup device unit 20 is filled by the welding section 35, the lens unit 10 and the image pickup device unit 20 are airtightly (watertightly) fixed without providing the bonding material 31 in the gap.

The invention described in the individual embodiments above is not limited to the embodiments and the modifications and can be variously modified without departing from the scope in an implementation phase in addition. Further, the individual embodiments described above include the inventions in various stages, and various inventions can be extracted by appropriate combinations in a plurality of disclosed constituent elements.

For example, even when some constituent elements are deleted from the entire constituent elements indicated in the individual embodiments, in the case that the described problem can be solved and the described effect can be obtained, the configuration from which the constituent elements are deleted can be extracted as the invention.

What is claimed is:

1. An image pickup unit provided in an endoscope, the image pickup unit comprising:
   a cylindrical lens holding frame configured to hold an objective optical system;
   a cylindrical image pickup device holding frame configured to hold an image pickup device including a light receiving section that detects an object image formed by the objective optical system, to which the lens holding frame is interpolated and fitted;
   a welding section formed at one location and a non-welding section provided on a fitting section of the lens holding frame and the image pickup device holding frame and formed at an outer circumferential section of the image pickup device holding frame on a same plane offset from an optical axis, configured to fix the lens holding frame and the image pickup device holding frame at a fitting position at which an image forming surface of the object image by the objective optical system and the light receiving section are made to coincide; and
   a bonding material configured to fill a gap formed between the lens holding frame and the image pickup device holding frame;
   wherein the lens holding frame has a hole section that holds the objective optical system, an outer diameter center of the fitting section and an inner diameter center of the hole section in the lens holding frame are separated by a predetermined distance, and the objective optical system is held so as to be eccentric in a predetermined eccentric direction to an outer diameter of the fitting section in the lens holding frame; and
   the welding section is formed in a direction opposite to the eccentric direction in the lens holding frame.

2. The image pickup unit provided in an endoscope according to claim 1, wherein the welding section is formed at a position on an extension line facing a position of a low image height in the light receiving section.

3. The image pickup unit provided in an endoscope according to claim 1,
   wherein, for the image pickup device holding frame, an inner diameter center of the fitting section in the image pickup device holding frame is separated from a predetermined image forming center position of the light receiving section by a predetermined distance in a predetermined first direction, and
   the welding section is formed in a direction opposite to the first direction in the image pickup device holding frame.

4. The image pickup unit provided in an endoscope according to claim 1,
   wherein a first planar section is formed at the fitting section of the lens holding frame, a second planar section to be abutted to the first planar section and brought into surface contact is formed at the fitting section of the image pickup device holding frame, and
   the welding section is formed at a position at which the first planar section and the second planar section are in surface contact.

5. An endoscope comprising the image pickup unit according to claim 1.

6. An image pickup unit provided in an endoscope, the image pickup unit comprising:
   a cylindrical lens holding frame configured to hold an objective optical system;
   a cylindrical image pickup device holding frame configured to hold an image pickup device including a light receiving section that detects an object image formed by the objective optical system, to which the lens holding frame is interpolated and fitted;
   a plurality of welding sections and a non-welding section provided on a fitting section of the lens holding frame and the image pickup device holding frame and formed at an outer circumferential section of the image pickup device holding frame on a same plane offset from an optical axis, configured to fix the lens holding frame and the image pickup device holding frame at a fitting position at which an image forming surface of the object image by the objective optical system and the light receiving section are made to coincide; and a bonding material configured to fill a gap formed between the lens holding frame and the image pickup device holding frame, wherein the lens holding frame has a hole section that holds the objective optical system, an outer diameter center of the fitting section and an inner diameter center of the hole section in the lens holding frame are separated by a predetermined distance, and the objective optical system is held so as to be eccentric in a predetermined eccentric direction to an outer diameter of the fitting section in the lens holding frame, and the welding sections are formed by welding one of the welding sections positioned in a direction opposite to the eccentric direction in the lens holding frame first among the welding sections in plurality.

7. An image pickup unit provided in an endoscope, the image pickup unit comprising:

a cylindrical lens holding frame configured to hold an objective optical system;

a cylindrical image pickup device holding frame configured to hold an image pickup device including a light receiving section that detects an object image formed by the objective optical system, to which the lens holding frame is interpolated and fitted;

a plurality of welding sections and a non-welding section provided on a fitting section of the lens holding frame and the image pickup device holding frame and formed at an outer circumferential section of the image pickup device holding frame on a same plane offset from an optical axis, configured to fix the lens holding frame and the image pickup device holding frame at a fitting position at which an image forming surface of the object image by the objective optical system and the light receiving section are made to coincide; and a bonding material configured to fill a gap formed between the lens holding frame and the image pickup device holding frame, wherein, for the image pickup device holding frame, an inner diameter center of the fitting section in the image pickup device holding frame is separated from a predetermined image forming center position of the light receiving section by a predetermined distance in a predetermined first direction, and the welding sections are formed by welding one of the welding sections positioned in a direction opposite to the first direction in the image pickup device holding frame first among the welding sections.

8. An image pickup unit provided in an endoscope, the image pickup unit comprising:

a cylindrical, lens holding frame configured to hold an objective optical system;

a cylindrical image pickup device holding frame configured to hold an image pickup device including a light receiving section that detects an object image formed by the objective optical system, to which the lens holding frame is interpolated and fitted;

a plurality of welding sections and a non-welding section provided on a fitting section of the lens holding frame and the image pickup device holding frame and formed at an outer circumferential section of the image pickup device holding frame on a same plane offset from an optical axis, configured to fix the lens holding frame and the image pickup device holding frame at a fitting position at which an image forming surface of the object image by the objective optical system and the light receiving section are made to coincide; and a bonding material configured to fill a gap formed between the lens holding frame and the image pickup device holding frame, wherein a first planar section is formed at the fitting section of the lens holding frame, a second planar section to be abutted to the first planar section and brought into surface contact is formed at the fitting section of the image pickup device holding frame, and the welding sections are formed by welding a position at which the first planar section and the second planar section are in surface contact first among the welding sections.

* * * * *